United States Patent
Kazys et al.

[11] Patent Number: 5,808,199
[45] Date of Patent: Sep. 15, 1998

[54] SYSTEM FOR MEASURING ULTRASONICALLY THE ELASTIC PROPERTIES OF A MOVING PAPER WEB

[75] Inventors: Rymantas J. Kazys, Kaunas, Lithuania; T. Patrick Stolpe, Alunda, Sweden

[73] Assignee: AB Lorentzen & Wettre, Kista, Sweden

[21] Appl. No.: 809,225

[22] PCT Filed: Oct. 5, 1995

[86] PCT No.: PCT/SE95/01145

§ 371 Date: Mar. 26, 1997

§ 102(e) Date: Mar. 26, 1997

[87] PCT Pub. No.: WO96/11396

PCT Pub. Date: Apr. 18, 1996

[30] Foreign Application Priority Data

Oct. 6, 1994 [SE] Sweden ................................. 9403384

[51] Int. Cl.⁶ .......................... G01N 29/18; G01N 29/24
[52] U.S. Cl. ............................. 73/597; 73/159; 73/644; 364/550
[58] Field of Search .......................... 73/597, 159, 644, 73/639; 364/550; 162/198, 263

[56] References Cited

U.S. PATENT DOCUMENTS

| | | | |
|---|---|---|---|
| 3,720,098 | 3/1973 | Dixon | 73/597 |
| 4,291,577 | 9/1981 | Baum et al. | 73/159 |
| 4,446,735 | 5/1984 | Weilacher | 73/597 |
| 4,574,634 | 3/1986 | Pappano | 73/597 |
| 4,688,423 | 8/1987 | Orkosalo | 73/159 |
| 4,730,492 | 3/1988 | Burk | 73/159 |
| 4,735,087 | 4/1988 | Hourani et al. | 73/597 |
| 5,014,547 | 5/1991 | Holroyd | 73/159 |
| 5,025,665 | 6/1991 | Keyes, IV et al. | 73/159 |
| 5,398,538 | 3/1995 | Williams et al. | 73/159 |
| 5,525,854 | 6/1996 | Hall et al. | 310/334 |

FOREIGN PATENT DOCUMENTS

| | | |
|---|---|---|
| 489018 | 6/1974 | Russian Federation . |
| 489036 | 6/1974 | Russian Federation . |
| WO 91/17435 | 11/1991 | WIPO . |

*Primary Examiner*—Hezron E. Williams
*Assistant Examiner*—Rose M. Miller
*Attorney, Agent, or Firm*—Burns, Doane, Swecker & Mathis, L.L.P.

[57] ABSTRACT

The invention relates to a system for measuring ultrasonically the elastic properties of a moving paper web. A noise type ultrasonic sound wave is generated by an ultrasonic sound generating device in the web at an excitation point. A reference ultrasonic wave reradiated into the air from the excitation point is indicated. A pick-up device is provided for receiving ultrasonic sound reradiated from the paper web at a predetermined distance form the location of the sound generating device. The ultrasonic sound generating device and the reference ultrasonic receiving device are provided on the same side of the paper web. At least one of these two kinds of devices includes a number of elements provided symmetrically in relation to the other device.

16 Claims, 7 Drawing Sheets

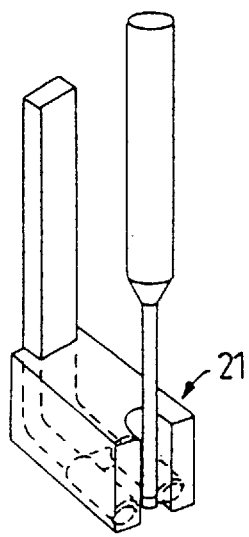
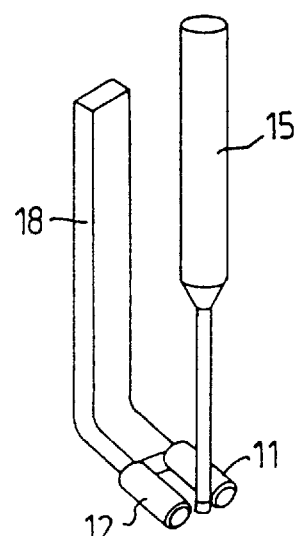
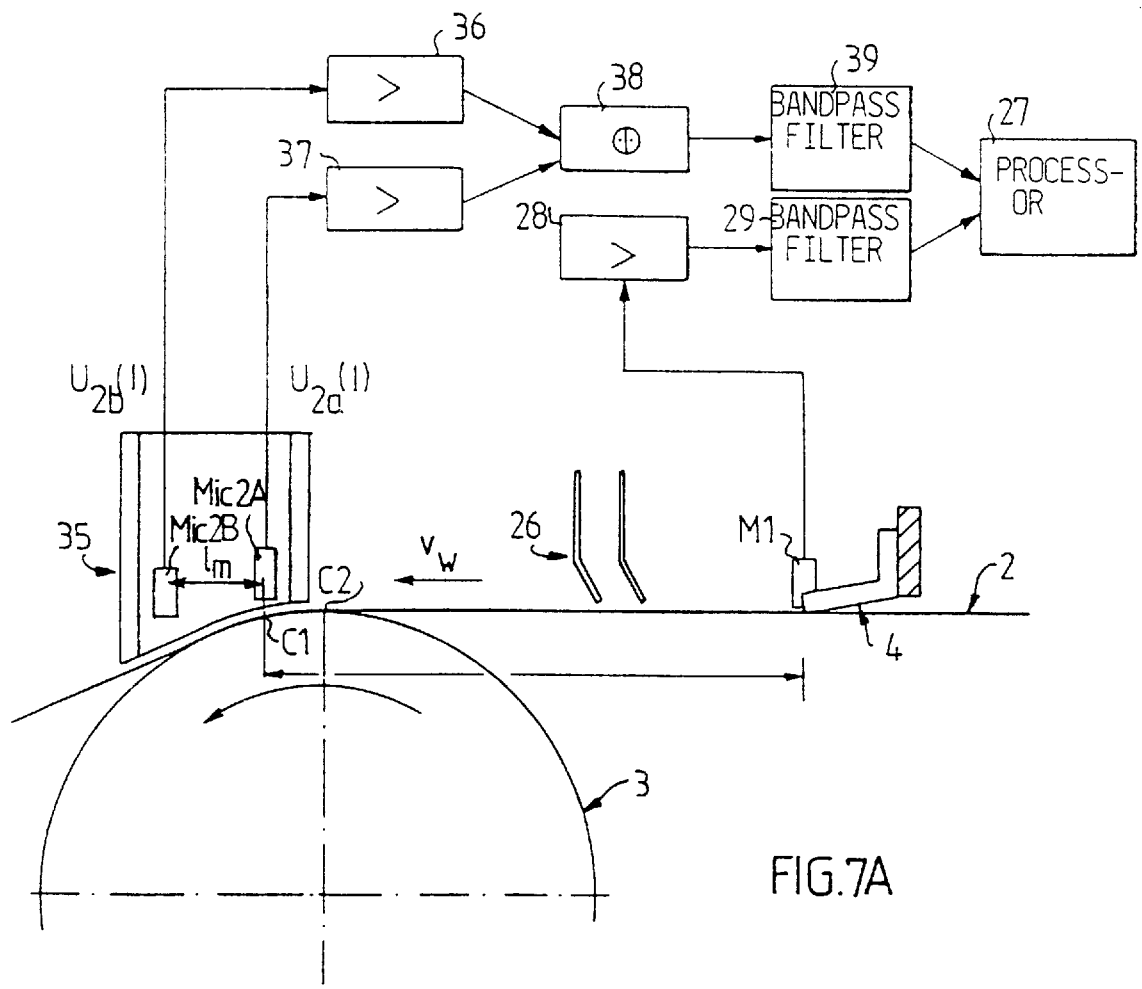

SYSTEM FOR MEASURING ULTRASONICALLY THE ELASTIC PROPERTIES OF A MOVING PAPER WEB

This invention concerns the measurement of the velocity of ultrasound, in-plane, for a moving paper web. The ultrasound velocity in paper is known to be related to various measures of paper strength and stiffness.

BACKGROUND OF THE INVENTION

The most important values for the papermaker to consider from ultrasound velocity measurements on paper web are:
TSO Tensile Stiffness orientation, i.e. the orientation of the elastic properties in-plane of the paper sheet,
$TSI_{MD}$ Tensile Stiffness Index in the machine direction of the paper machine,
$TSI_{CD}$ Tensile Stiffness Index in the cross direction of the paper machine.

It is possible to determine these quantities and also the anisotropy ratio $TSI_{MD}/TSI_{CD}$ by performing the ultrasound velocity measurements in the machine direction (MD), cross direction (CD) and directions between (MD) and (CD). The tensile stiffness and anisotropy ratio characterize the paper quality.

The velocity of an ultrasonic pulse propagating in-plane of a paper sheet corresponds with the sheet's elastic properties, i.e. the TSI. TSI can be compared to Young's modulus (or "Emodulus") for other materials. The relationship can be expressed by:

$$TSI = v^2 * c$$

where TSI is measured in kNm/g, v is the propagation velocity (km/sek) for the ultrasonic pulse, and c is a dimensionless constant close to 1 depending on Poisson's ratio for the paper. The velocity is easily determined by measuring the propagation time for an ultrasonic pulse between a transmitter and a receiver.

These quantities are often measured statically on samples taken from a paper web. However, it is desirable to measure these paper qualities on-line by an on-line meter used as a sensor for the continuous control of a paper manufacturing process.

Most of the known on-line meter arrangements (U.S. Pat. No. 4,291,577, U.S. Pat. No. 4,688,423, U.S. Pat. No. 4,730,492) employ rotating wheels, which contain transmitters and receivers of ultrasonic waves. These wheels are rotated by a moving paper web, that requires a direct physical contact between the wheels and the web. The ultrasound velocity is usually determined from the delay time of an ultrasonic signal between the particular transmitter and receiver.

In order to obtain a reasonable measurement accuracy the wheels must by synchronized which makes the system extremely complicated and unreliable. An arrangement described in U.S. Pat. No. 4,688,423 overcomes this drawback by employing disk type transducers which can be excited continuously and, therefore, synchronization of the wheels is not necessary. However, the arrangements described in the above-mentioned patent specifications need a direct mechanical contact between the ultrasonic transducers and the web.

In a papermaking machine the fast moving web vibrates in the direction normal to the web surface, creating a randomly changing force applied to the wheels. The amplitude of excited and received ultrasonic waves depends on the pressure between particular ultrasonic transducer and the web. Due to the randomly changing force, the amplitudes of received signals fluctuate, thereby making the results of measurements less accurate.

The physical contact with the web is not needed if ultrasonic waves are excited and detected optically, as described in U.S. Pat. No. 5,025,665. Ultrasonic waves in the paper web are generated by means of a laser. This wave is detected at a determined distance from the excitation point by means of another laser beam, reflected from the web. The velocity of the ultrasonic wave is obtained from the measured delay time between the excitation instant and the time of the wave arrival.

The disadvantage of this optical system is that the amplitudes of the ultrasonic waves propagating in-plane of the web are very small. A very strong acoustic noise exists in papermaking machines, which is accompanied by the vibrations of the moving web. In fact this makes the optical detection of the lowest order symmetrical Lamb waves impossible, and only these waves are suitable for measurements of the stiffness and tensile strength of paper.

A method and device for continuously determining the modulus of elasticity of advancing flexible material, such as paper web, in a contactless fashion is disclosed in WO91/17435. An ultrasonic wave train is transmitted through the air towards the web. The ultrasonic waves scattered through the air by the material are sensed at a distance d, about tventy to fourty centemeters from the transmission point at the same side of the web, no reference ultrasonic wave receiving means being provided for receiving a reference ultrasonic wave from the transmission point.

Other prior on-line paper measuring systems are disclosed in the U.S.S.R. Pat. No. 489018 and U.S.S.R. Pat. No. 489036, and described in the publication by Kazys (the inventor of the present invention), Proceedings of 20th international conference on Acoustics, Praque, 1981, p.p. 6–10. The ultrasound velocity in a moving paper web was determined by exciting broad band noise-like ultrasonic wave by means of dry friction, receiving the ultrasonic wave reradiated by the web by two non-contacting ultrasonic receivers and calculating the cross-correlation function between these two received signals.

The first receiver was placed opposite to the ultrasonic transmitter and the second at a determined Distance from the transmitter along the web.

In order to improve the signal/noise ratio, a rotating cylinder was placed underneath the web close to the second ultrasonic receiver. The delay time was determined from the delay of the peak value of the cross-correlation function. The advantage of this measuring system compared to the ones described above was that it had no moving or rotating parts involved in the active measuring facilities.

The disadvantages of the measuring system described in the above-mentioned USSR-patents are that the excitation and reception of the ultrasonic waves are performed from the opposite sides of the web. Also, the signal/noise ratio is not sufficient high enough to permit reliable continous on-line measurements in a mill environment. Another problem which is encountered in performing measurements in other directions than the web propagation direction is an even worse signal/noise ratio due to the higher losses of ultrasonic waves in an anisotropic material.

The main object of the present invention is to provide an on-line measuring system with single side access to the paper web, performing measurements at different directions in-plane of a moving web.

Another object of the present invention is to provide an on-line measuring system having improved in noise robustness for the system in a paper mill environment.

Still another object is to provide an on-line dust-insensitive measuring system.

Yet another object is to provide an on-line measuring system providing well-defined and precise measuring results.

These objects are achieved with a system having the characterizing features disclosed in the main claim. Further features and further developments of the invention are disclosed in the subclaims.

SUMMARY OF THE INVENTION

The present invention solves the problems associated with the prior art and other problems by providing a system for continuous measurements of the velocity of ultrasonic waves in a moving paper web. The foregoing is accomplished by exciting a broad-band noise type Lamb wave in the web by having the source of ultrasonic waves and all the ultrasonic receivers placed on a single side of the web. The broad band noise-like Lamb wave in the paper web is generated by means of dry friction between the moving web and the friction head. The system has no moving parts and all signals are received by non-contacting means.

The delay time of the ultrasonic wave is preferably determined as a zero cross of the Hilbert transform of the cross-correlation function of the received signals, corresponding to the maximum value of the cross-correlation function.

In order to make the system noise robust, i.e. provide a low signal/noise ratio, the receiving of the reradiated ultrasonic waves is performed above the rotating cylinder of a paper making machine at the particular position in respect to the line, where the moving web touches the cylinder for the first time. The pick-up is preferably made by two microphones having such a distance from each other that airborne ultrasound waves from the friction head are reduced and ultrasound waves propagating through the paper web are enhanced.

BRIEF DESCRIPTION OF THE DRAWINGS

For a more complete understanding of the present invention and for further objects and advantages thereof, reference is now made to the following description taken in conjunction with the accompanying drawings, in which:

FIGS. 4A, 4B and 5A, 5B and 6A, 6B illustrate different embodiments of friction head and microphone units, FIG. 7A illustrates schematically a side view of a second embodiment of a measuring system according to the invention.

With reference to FIG. 1, a prior art on-line paper measuring system disclosed in the U.S.S.R. Pat. No. 489018 includes a friction head 1 provided on one side of a moving paper web 2 generating a noise-like ultrasonic signal $v_w$ as a result of dry friction between the head 1 and the web 2. A random signal with a normal law of distribution up to 70 to 90 kHz is excited. The part of this signal $v_w$ propagating in the paper web 2 as the zero order symmetrical Lamb wave $s_0$ is the interesting one to examine. The excited wave is reradiated partially into the surrounding air and is picked up by a contactless reference microphone Mic1 provided opposite the head 1 on the other side of the web 2, and by a contactless pick-up microphone Mic2 provided on the same side of the web as the reference microphone Mic1 but a determined distance $l_0$ away from, i.e. downstream from, the head 1 along the web in its moving direction, below called "the machine direction". In order to have an enhanced reradiation of the propagated wave from the web to the air the web 2 is supported by a rotating cylinder 3 opposite the pick-up microphone Mic2. The signals from the microphones Mic1 and Mic2 are fed to a processing unit 4', which correlates the two signals in order to derive the propagation time through the web, so that the velocity of the ultrasonic wave in the paper web can be computed and the results presented on a display 5'.

From a commercial point of view, a measuring system in which all units are located at the same side of a paper web has many advantages. However, in order to implement one side access approach it is necessary to overcome a lot of problems.

1. According to prior art, the reference microphone could not be put at the same distance from a signal source as the pick-up microphone is from a paper web, because both the reference microphone and the signal source had to be located on the same side of the web. For the same reason the reference microphone surface usually could not be perpendicular to a propagation direction of the signal in air, and that caused a significant reduction in a normalized cross-correlation (covariance) function value or a distortion of its shape.

2. The location of the signal source unit and both the reference microphone and the pick-up microphone for the waves propagated along the web on the same side creates a direct wave propagating in air that is much stronger than in the case of a two-side access, because then the paper web is not shielding the airborne ultrasonic wave. It reduces a degree of correlation between the transmitted and received signals too.

3. The friction head causes an abrasion of the paper and scrapes off fibres which produces dust. If it is placed on the same side of the web as the microphones this dust will be transported to the microphones, which will reduce noticeably their sensitivity and distort their frequency response, if the same kind of friction heads are used as in prior art.

Figure 1:
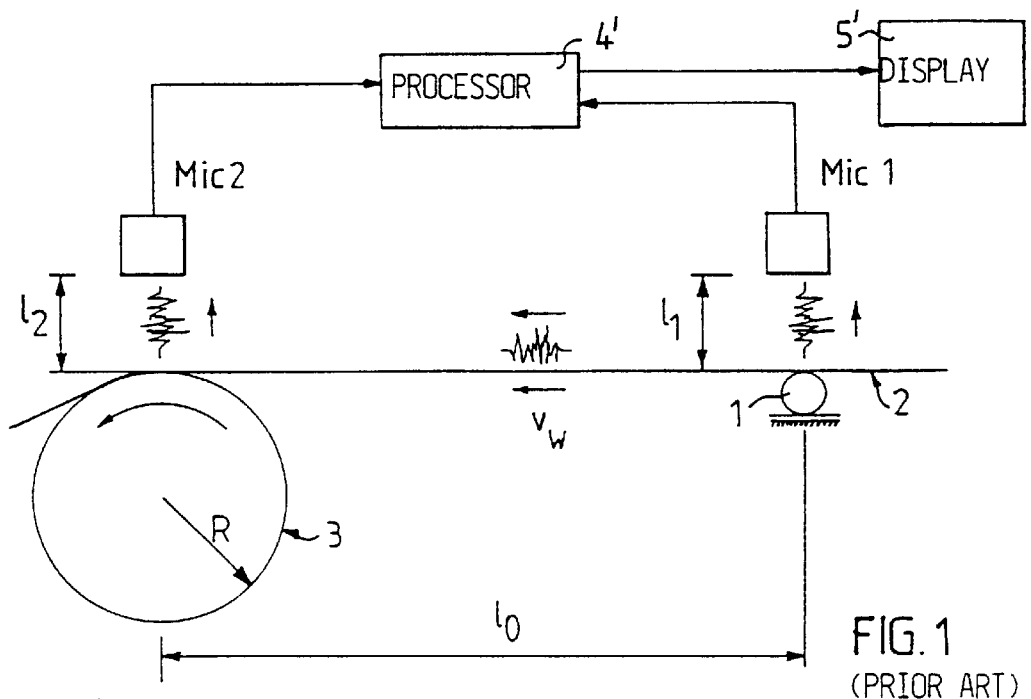
FIG. 1 illustrates schematically a measuring system according to the prior art.
Figure 2:
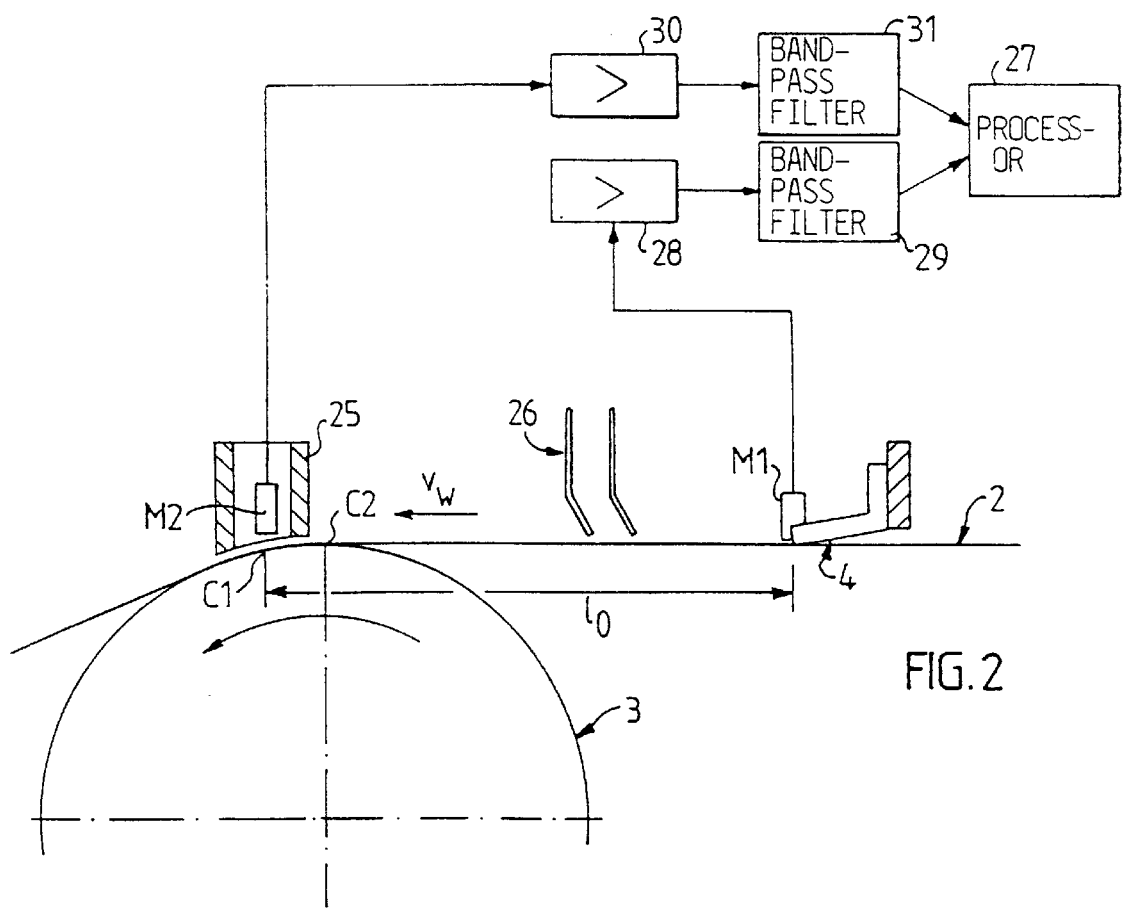
FIG. 2 illustrates schematically a first embodiment of a measuring system according to the invention.

Therefore, a new kind of friction head 4 adapted to a reference microphone M1 is provided according to the invention illustrated schematically in the embodiments of the invention shown in FIGS. 2 and 6.

The main feature of the combination of the friction head 4 and the reference microphone M1 is that friction and microphone elements are provided symmetrically to each other. This means that there could be one friction element and an even number of microphone elements provided symmetrically in relation to the friction element such that the microphones in each pair have the same distance to the friction element, or there could be one microphone element and an even number of friction elements placed around the microphone element. The friction elements have preferably a nearly pointlike contact with the paper web.

Figure 3A:
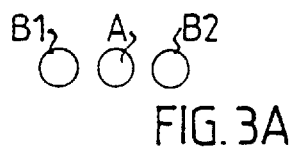
FIG. 3A and 3B illustrates different friction head/microphone combinations.
Figure 3B:
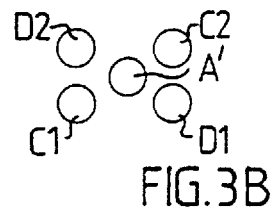

FIG. 3A shows a first embodiment of the friction head/reference microphone combination in which one element A of the first kind is provided between two elements B1, B2 of the other kind. FIG. 3B shows another embodiment in which one element A' of the first kind is surrounded by four elements C1, C2 and D1, D2 of the other kind, each pair C1, C2 and D1, D2 being placed diagonally in relation to the first kind of element A'. From a practical point of view the element A or A' is preferably a microphone element, since then it is not necessary to balance the signals from several elements. However, friction elements will cause dust in the environment and measures must be taken to minimize the influence of dust on the microphone(s). Thus, the prefered embodiment, shown in FIG. 3A, is to have a microphone between two pointlike friction elements placed along a line perpendicular to the machine direction, i.e. the moving direction of the paper web. If more than two friction elements are provided they must all be provided at the side of a line through an ultrasonic sound receiving element of the reference means directed in the machine direction of the moving paper web in order to prevent dust from coming directly onto the microphone.

Figure 4A:
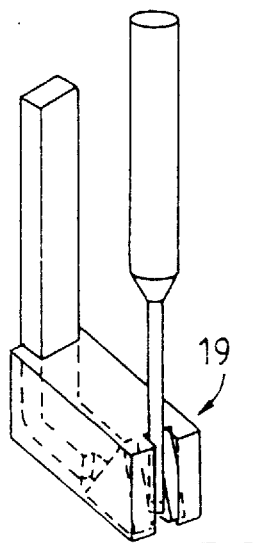

Three embodiments of the unit of the friction head and reference microphone having the preferred configuration mentioned above are shown in FIGS. 4A, 4B and 5A, 5B and 6A, 6B, respectively. The FIGS. 4A, 5A, and 6A show the actual appearance of the units when a noise shield is provided in order to minimize air borne sound waves from reaching the microphone, and the FIGS. 4B, 5B, and 6B show the units without the noise shield.

Figure 4B:
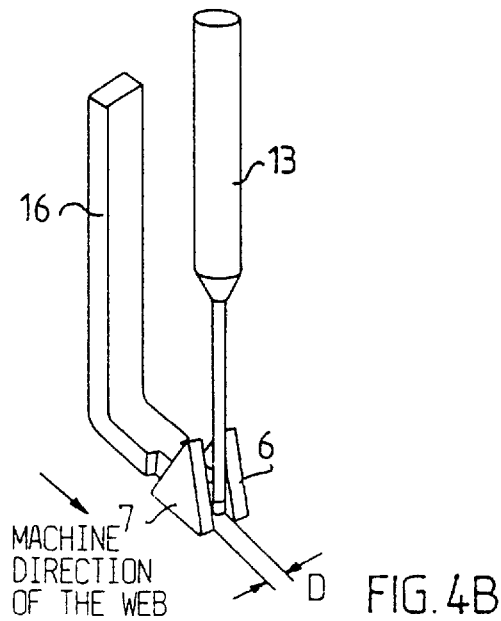
Figure 5A:
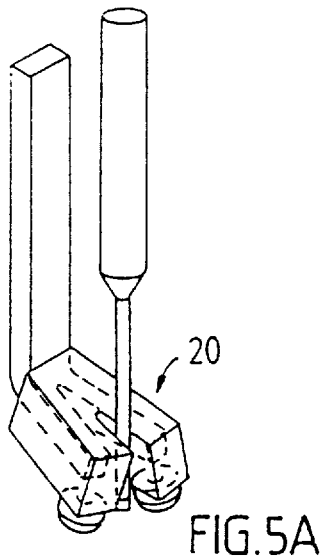
Figure 5B:
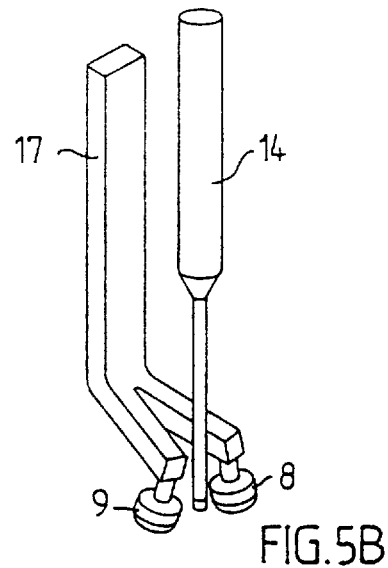
Figure 8A:
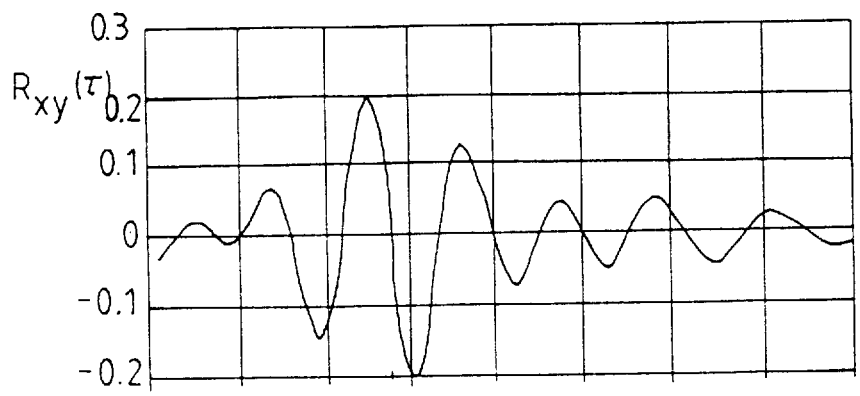
FIGS. 8A to 8D are diagrams of signals provided in different operation steps in searching for the delay time of the ultrasonic wave transmitted through the paper web.
Figure 8B:
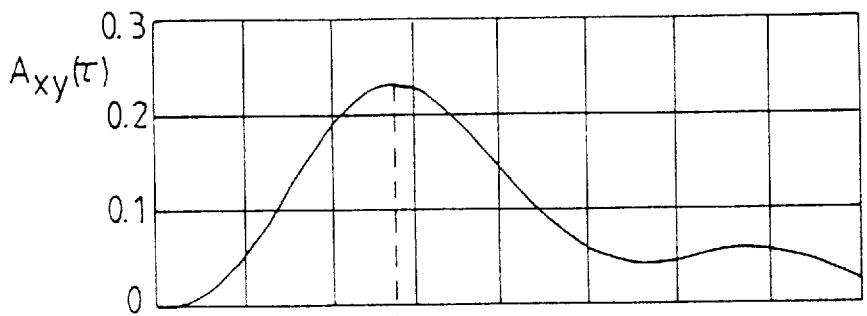
Figure 8C:
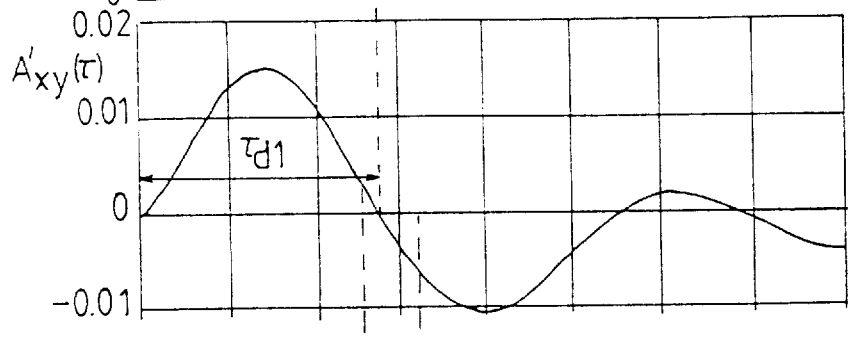
Figure 8D:
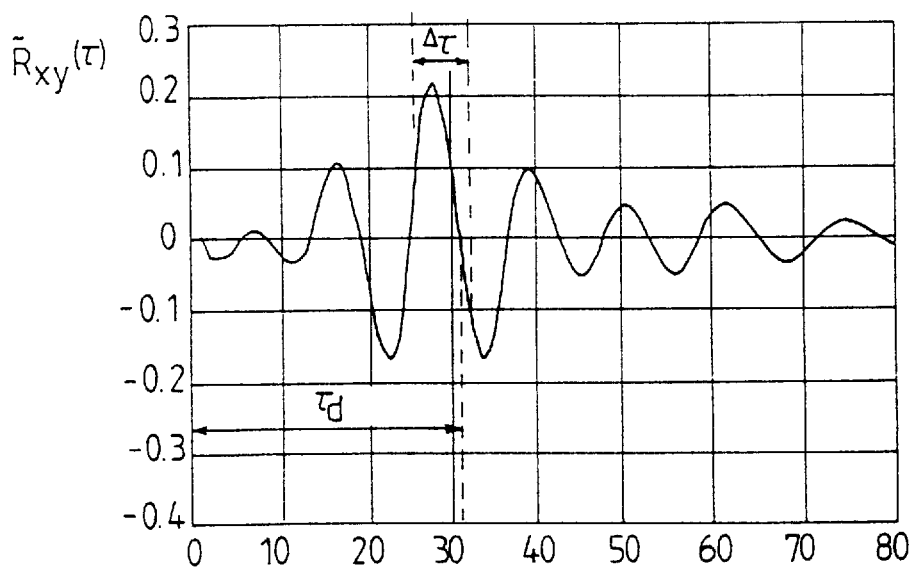
Figure 9:
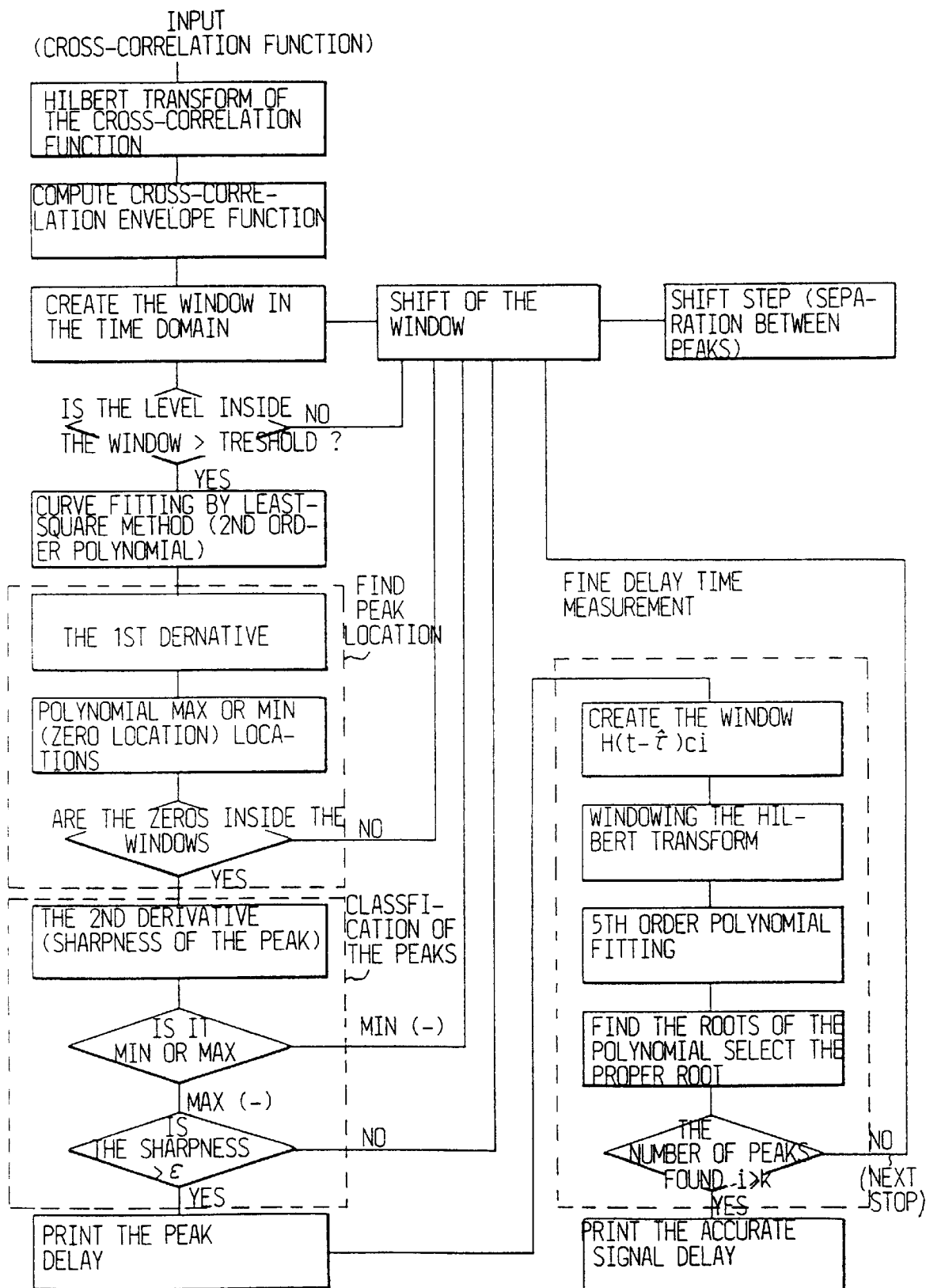
FIG. 9 is a flow chart of the processing operation in order to provide the delay time of the ultrasonic wave in-plane of the paper web, The same references are used for the same elements in the Figures.

Two friction parts, 6, 7 in FIG. 4B, 8, 9 in FIG 5B, and 10, 11 in FIG. 6B, are placed such that their contact point with the paper web is provided on each side of the ultrasonic reference microphone 13, 14 or 15, respectively, along a line perpendicular to the machine direction of the web. The friction parts are preferably made from a hard alloy material, for instance tungsten carbide. The friction parts are held by a holder 16, 17 or 18, respectively.

The distance D between the friction parts is much less than the wavelength of the ultrasonic wave in the web. Also, the dimensions of the contact area between the friction parts and the paper web are less than the wavelength of the ultrasonic wave in the web. Thus, this kind of friction source acts substantially like a two-point-source. The distance between the contact areas and the plane of the reference microphone is comparable with the wavelength in air for the generated ultrasonic waves (for $f_0$=40 kHz, $\lambda_a/2$=4.3 mm, where $f_0$ is the center frequency of the signal spectrum, and $\lambda_a$ is the wavelength of the center frequency in air).

The signals provided in the web by the friction parts are captured by the reference microphone M1 provided as close as possible to the middle point between the friction parts. In order to reduce the waves radiated not by the contact area by the friction parts and transmitted through the air to the reference microphone M1 the noise shield 19, 20 and 21, respectively, is placed around the friction parts and held by their holder and is provided with an opening adapted to hold the reference microphone in place. The noise shield also protects the microphone from at least some of the dust caused by the friction between the parts and the web, and this effect is enhanced if the noise shield has its sides turned towards the microphone somewhat nearer to the web than its outer sides thus directing the dust outwardly.

Each of the two parts 6, 7 of the friction head in FIGS. 4A and 4B has a triangular form having its base angled to the paper web. This friction head provides the best measuring result but it scratches the paper. Each of the two parts 8, 9 of the friction head in FIGS. 5A and 5B are formed as hemispheres, which has a substantially lesser affect on the paper web than the head in FIGS. 4A, 4B; however, the measuring result is satisfying but not as good as from the head 6, 7. The friction parts 8, 9 are made of hard alloy and comprise tips, contacting the web, covered by a material absorbing ultrasonic waves, for example, a soft rubber. Each of the two friction parts 11, 12 of the friction head in FIGS. 6A and 6B are formed as rounded pins angled to the web and could be seen as a compromise between the other two embodiments of the friction head as regards scratching the paper web and providing well distinguishable signals through the web.

Returning to FIG. 2, the signal part of the ultrasonic wave $v_w$ transmitted through the web of interest to be indicated is the $s_0$ wave signal, which corresponds to the symmetric zero order Lamb waves propagated in the web 2, i.e. the fastest propagating wave. The so wave reradiated from the web is captured by a pick-up microphone M2 located opposite to the contact line C1 between the rotating cylinder and the web 2 from which the best reradiation into the air of the $s_0$ wave propagated in the web is provided.

The lateral dimension of the pick-up microphone M2, and also of the reference microphone M1, are at least 10 times less than a wavelength of the ultrasonic wave in the paper web, and the microphones are placed at a distance from the web less than a wavelength of the ultrasonic wave $s_0$ reradiated by the web into air.

Noise is also radiated into the air from the contact line $C_2$ where the web 2 first meets the cylinder 3. This noise should preferably be suppressed as far as possible and therefore a noise suppressing shield 25, for example made of rubber, is provided around the microphone M2 shielding it from the noise from the contact line $C_2$ and also from ambient noise. Thus, its outer edge nearest to the contact line $C_2$ is located downstream of this line. The shield has a small inner diameter so that the microphone M2 is placed close to its internal edge.

In order to make an extra shield for the microphone M2 both regarding the airborne noise from the friction head and against the dust from it a number of shields 26 are provided above the paper web between the microphone M1 and the rotating cylinder 3.

The signal from the reference microphone M1 is fed to a first input of a processor 27 through an amplifier 28 and a bandpass filter 29. The signal from the pick-up microphone M2 is fed to a second input of the processor 27 through an amplifier 30 and a bandpass filter 31. The processor 27 will make a cross-correlation operation on the signals from the two microphones. Preferably this operation will include a Hilbert transform. An example of this kind of operation will be given below in connection with the embodiment shown in FIG. 7. The example given there for the somewhat more complicated embodiment could easily be amended to be adapted to the embodiment in FIG. 2 by a person skilled in the art.

In accordance with the invention measures are taken to enhance the signal/noise ratio of the correlated signals, particularly in a noisy environment. Therefore, in accordance with a second embodiment of the invention, shown in FIG. 7A, a double channel measuring receiving microphone device is provided to receive the wave propagated along the web 2. It is, however, to be noted that more than two pick-up microphones can be provided according to the invention.

In the second embodiment of the invention at least two pick-up ultrasonic microphones Mic2A and Mic2B, being the pick-up elements of the pick-up receivers, are placed a distance $1_m$ from each other, the distance being chosen to be a half-wavelength of the wave in air at the centre frequency of the bandwidth of the ultrasonic wave transmitted through the web. The microphone Mic2A is located opposite the contact line $C_1$. The microphone Mic2B is located on the side of the microphone Mic2A turned away from the friction head 4.

Thus the principle of the operation is based on a difference of ultrasound velocities in air ($v_a$=343 m/sek) and paper ($v_{s0}$ 1.5 to 4 km/sek). The signals at the outputs of the microphones Mic2A and Mic2B are given by:

$$u_{2a}(t)=y_s(t)+y_a(t)+n_{md}(t)n_{0a}(t)$$

$$u_{2b}(t)=k_s{}^*y_s(t-\Delta t_s)+k_a{}^*y_a(t-\Delta t_a)+k_n{}^*n_{md}(t+\Delta t_a)+n_{0b}(t)$$

where $u_{2a}(t)$ and $u_{2b}(t)$ are the complete wave signal at the output of the microphones Mic2A and Mic2B, respectively, $y_s(t)$ is the $s_0$ wave signal at the output of the microphone Mic2A, $y_a$ is the airborne wave generated by the friction head, $n_{md}$ is the noise propagating along the machine direction at the output of the microphone, $n_{0a}(t)$ and $n_{0b}(t)$ are electronic noise and ambient noise propagating along directions others than the machine direction, $k_s$, $k_a$, and $k_n$ are the coefficients reflecting the asymmetry of the microphones Mic2A and Mic2B for the appropriate waves, $\Delta t_s = l_m/v_{s0}$ is the delay time of the $s_0$ wave between the microphones, and $\Delta t_a = l_m/v_a$ is the delay time of airborne waves between the microphones propagating along the machine direction.

Due to extensive differences in the ultrasonic velocities in the web and in air, $\Delta t_s \ll \Delta t_a$, $\Delta t_s < t_0$, $t_0 = 1/f_0$, where $f_0$ is the center frequency of the signal spectrum. Therefore, the spectral components with frequencies equal or close to frequency $f_0$ are approximately:

$$y_s(t) \approx y_s(t - \Delta t_s)$$
$$y_a(t) \approx -y_a(t - \Delta t_a)$$
$$n_{md}(t) \approx -n_{md}(t + \Delta t_a)$$

Then, addition of the signals from the two microphones Mic2A and Mic2B gives the following result:

$$u_2(t)=u_{2a}(t)+u_{2b}(t)=(1+k_s)^*y_s(t)+(1-k_a)^*y_a(t)+(1-k_n)^*n_{md}(t)+n_{0a}(t)+n_{0b}(t)$$

The coefficients $k_s$, $k_a$, $k_n$ are close to 1, which gives approximately:

$$u_2(t)=2^*y_s(t)+\epsilon_a y_a(t)+\epsilon_n n_{md}(t)+[n_{0a}(t)+n_{0b}(t)]$$

where $\epsilon_a$ and $\epsilon_n$ are much lower than 1, which indicates that the amplitude of the $s_0$ wave signal is amplified twice and the amplitudes of the wave propagating in air along the machine direction from the friction head is substantially reduced, like the noise propagating in the machine direction. The electronic noises or the noises arriving from directions different from the machine direction are not suppressed and are added as partially correlated or uncorrelated random processes.

It is to be noted that the distance $l_m$ between the pick-up microphones could be chosen in another way, but then the equations above and the combination of them will be changed. The main feature of the choise of distance is that the term $y_s(t)$ is essentially enhanced and the term $y_a(t)$ essentially reduced in the combination.

Also, as in the embodiment shown in FIG. 2, a noise reducing shield 35, for instance of rubber, is placed around the microphones Mic2A and Mic2B in order to reduce the noise from the noisy surroundings. The shield 35, having the same function as the shield 25 in the embodiment shown in FIG. 2, has preferably, the shape of its lower side adapted to the shape of the paper web when it is transferred over the rotating cylinder 3, and has its wall placed quite close to the microphones Mic2A and Mic2B.

Referring now to the embodiment having the pick-up microphones placed one half-wavelength of the airborne ultrasonic wave apart, in order to estimate the velocity of the $s_0$ wave a cross-correlation should be made on the signals from the reference microphone M1 and the added signals from the two pick-up microphones Mic2A and Mic2B. The signals from the pick-up microphones are amplified in respective amplifiers 36 and 37 and then added in an adder 38. The signal from the adder 38 is fed to the second input of the processor 27 through a bandpass filter 39.

The processor 27 is provided with a program for performing an automatic time delay measurement in order to obtain the velocity of the wave in the actual paper web.

The delay time is determined from the cross-correlation function. For this purpose two methods are combined, namely, cross-correlation function envelope peak detection for a coarse evaluation and zero-crossing detection of the cross-correlation function Hilbert transform for the accurate measurements. Time diagrams illustrating this technique are given in FIGS. 8A to 8D. This techique is efficient in the case of relatively narrow-band signals, i.e., when a cross-correlation function has an oscillating character.

Therefore, as shown in FIG. 8A a cross-correlation function $\hat{R}_{xy}(\tau)$ between transmitted and received $s_0$ wave signal at the outputs of the receivers M1, 28, 29, and Mic2A, Mic2B, 36, 37, 38, 39 is provided $$R_{xy}(\tau)=(1/T)\int[x(t)+n_1(t)]^*[2y_a(t+\tau)+\epsilon[y_a(t+\tau)+n_{md}(t+\tau)]+n_2(t+\tau)]dtO$$

where T is the signal duration used for calculation, x(t) and y(t+$\tau$) are the signals from input channel M1, 28, 29, and the output channel Mic2A, Mic2B, 36, 37, 38, 39, respectively, and $n_1(t)$ is the noise received by the microphone M1 and $n_2(t+\tau)$ is the added noise received by the micropones Mic2A and Mic2B.

A zero-cross of the Hilbert transform of the cross-correlation corresponding to the maximum value of the cross-correlated function is made.

Then, the envelope, as shown in FIG. 8B, of a cross-correlation function Rxy($\tau$) is obtained by means of the Hilbert transform:

$$A_{xy}(\tau)=\sqrt{[R^2_{xy}(\tau)+\tilde{R}^2_{xy}(\tau)]}$$

(see FIG. 8C), where $$\tilde{R}_{xy}(\tau) = H[R_{xy}(\tau)] = \int_{-\infty}^{\infty} R_{xy}(t)/[\pi * (\tau - t)]dt$$

is the Hilbert transform of a cross-correlation function $\tilde{R}_{xy}(\tau)$ and shown in FIG. 8D. FIG. 8C shows the detection of the envelope peak shown in FIG. 8B.

In the presence of signals propagating through multiple paths, the cross-correlation function has a few peaks, corresponding to different delays. Then the envelope function can be presented as $$A_{xy}(\tau) = \sum_{i=1}^{N} A_i(\tau - \tau_{di})$$

where $\tau_{d1}, \tau_{d2} \ldots$ are the delays in the corresponding paths. Therefore, in a general case not just one but a few peaks will be detected. The proper peak is found by taking into account prior knowledge of the expected time of arrival, and usually is that closest to the zero instant.

The obtained rough estimate of the delay time $\hat{\tau}_{d_i}$ is used to produce a window H(t) in a time domain the width of which $\Delta\hat{\tau}$ is slightly less than half a period of oscillation of the band-limited cross-correlation function $$\Delta\tau < t_0/2$$

The window is located symmetrically in respect to the determined delay time $\hat{\tau}_{d_i}$ $$H(t - \hat{\tau}_{d_i}) = \begin{cases} 1, \text{ for } \hat{\tau}_{d_i} - (\Delta\tau/2) \leq t \leq \hat{\tau}_{d_i} + (\Delta\tau/2) \\ 0, \text{ otherwise} \end{cases}$$

The accurate delay time estimation is obtained from the windowed Hilbert transform $R_w(t)$ of the initial cross-correlation function:

$$R_w(t) = H(t - \hat{\tau}_{d_i}) * \tilde{R}_{xy}(t)$$

The peak value of the envelope function $A_{xy}(\tau)$ corresponds to the peak value of the cross-correlation function $R_{xy}(\tau)$ only in the case of non-dispersive propagation. As it was noted above, the symmetrical $s_0$ wave used for the measurements propagates without noticeable dispersion. On the other hand, the uncertainty in detecting the rough delay time should be less than $t_0/2$.

For a 35 kHz center frequency, rough delay time uncertainties of as much as $t_0/2 = 14\,\mu s$ can be allowed. Usually this requirement is easily fullfilled and no ambiguity occurs.

The peak values of the cross-correlation function $Rxy(\tau)$ correspond to the zero values of the Hilbert transform $\tilde{R}_{xy}(\tau)$. Hence, the time of signal arrival now can be found using simple zero-crossing technique (FIG. 8D):

$$R_w(t)_t = \tau_{d1} = H(t - \hat{\tau}_{d_i}) * \tilde{R}_{xy}(\tau) = \tau_{d1} = 0$$

It is worthwhile to remember, that by shifting the window function H(t) to the locations of other envelope peaks $\hat{\tau}_{d_i}$, the accurate delay times of signals propagating through different paths may be automatically determined.

A flowchart of a program in the processor 27 for automatically deriving the time delay is shown in FIG. 9 and includes shifting of the window $\Delta\tau$, shown in FIG. 8D, in several steps in order to find the searched time delay $\tau_d$ for the paper web 2.

The algorithm consists of three main stages: cross-correlation envelope function fitting by 2nd order polynomial; finding the peaks; and finding their classification according to a sharpness.

The algorithm starts from the window generation in the time domain. The width of the window is given in terms of sampling points and defines the number of points used in the analysis. The window is shifted step by step in subsequent algorithm loops. The size of this step defines the separation between two neighbouring peaks and can be chosen in such a way that minor peaks caused by a random noise or spurious waves would be ignored.

The cross-correlation envelope function fitting is needed for finding the peak and is performed by the least-square method using the 2nd order polynomial. Such a polynomial can have a positive or negative curvature depending on what kind of local extremity—a peak or a minimum has been found.

Strictly speaking, the 2nd order polynomial fitting always finds a local minimum or maximum independently of how they were created—by delayed signals or by random noise fluctuations. The influence of local fluctuations can be reduced by increasing the width of the window. Then the peaks caused by delayed waves are usually sharper than the other, spurious, peaks.

Therefore, the peak finding procedure consists of the first order derivative calculation, which enables the determination of the locations of all extremities and the 2nd order derivative calculation, which allows sorting them into maximums and minimums and, consequently, selection of the proper peak (or peaks) according to its (or their) sharpness. The sharpness $\epsilon$ is given by $\tau di$ the magnitude of the 2nd derivative of the peak.

The delay time estimate $\tau_{di}$ obtained from this peak is used to generate the window H(t) mentioned above.

The Hilbert transform of the cross-correlation function $R_{xy}(t)$ is multiplied by the windowing function H(t). All these functions are discrete in the time domain. The spacing between two adjacent points is equal to the sampling period $\Delta\hat{\Delta}t_s$. In order to obtain measurement errors less than the signal sampling interval $\Delta t_s$, the segment of the Hilbert transform is fitted using the least-square method by the 5th order polynomial. Then the Equation has five roots, but only the root inside the created window is selected. This root is a fine time delay $t_{di}$ estimation. The wave velocity $v_0 = l_0/t_{di}$, and the tensile stiffness $TSI = c_1 * v_0^2$, where $c_1$ is a dimensionless constant close to 1 depending on Poisson's ratio for the paper. The flowchart in FIG. 8 is believed to be self-explanatory and is therefore not described in further detail.

It is necessary to point out that if the peak of the cross-correlation function caused by the $s_0$-Lamb wave is the biggest, then the envelope function fitting can be omitted and the rough estimate of the peak delay obtained directly from the measured cross-correlation or envelope function. The other steps in the algorithm remain the same.

The method above has been described for measurement of the time delay in the machine direction and this will give the tensile stiffness index $TSI_{MD}$ in the machine direction of the paper machine. The friction head 4, the microphones M1, Mic2A and Mic2B are then located in line with the machine direction. However, as mentioned in the introductory part of the specification the tensile stiffness index $TSI_{CD}$ in the cross direction of the paper machine, and in directions between $TSI_{MD}$ and $TSI_{CD}$, are also needed in order to calculate the anisotropy ratio and the tensile stiffness orientation. An embodiment for also providing these quantities will now be described with reference to FIGS. 7B and 7C, even though the same feature naturally can also be provided for the embodiment shown in FIG. 2.

Figure 7C:
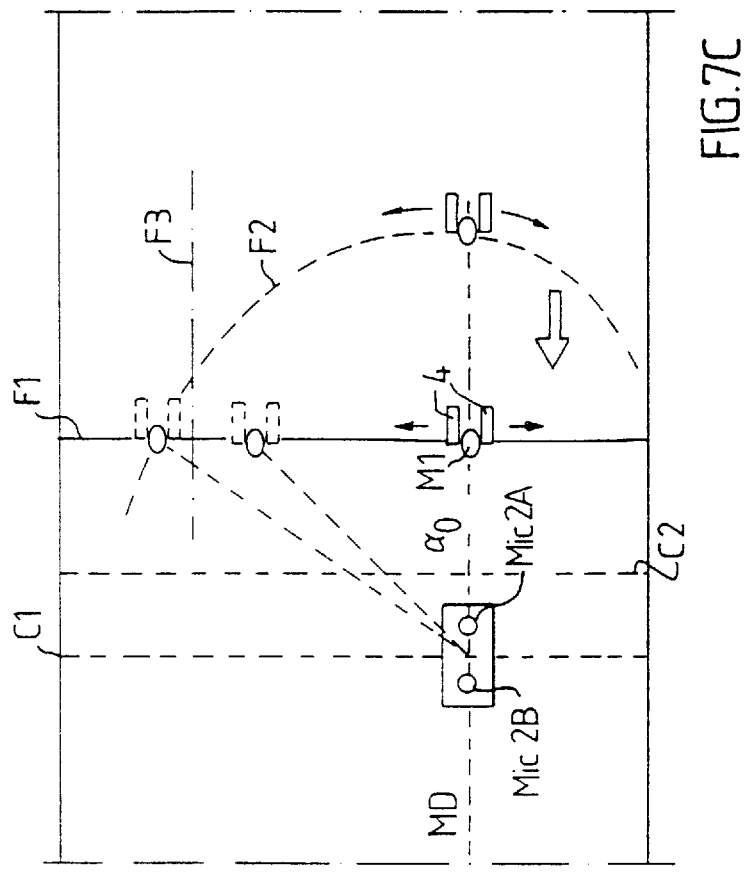
FIGS. 7B and 7C illustrate a schematic view from above of two embodiments of the system i FIG. 7A having the possibility of measuring the ultrasound velocity in different directions.
Figure 7B:
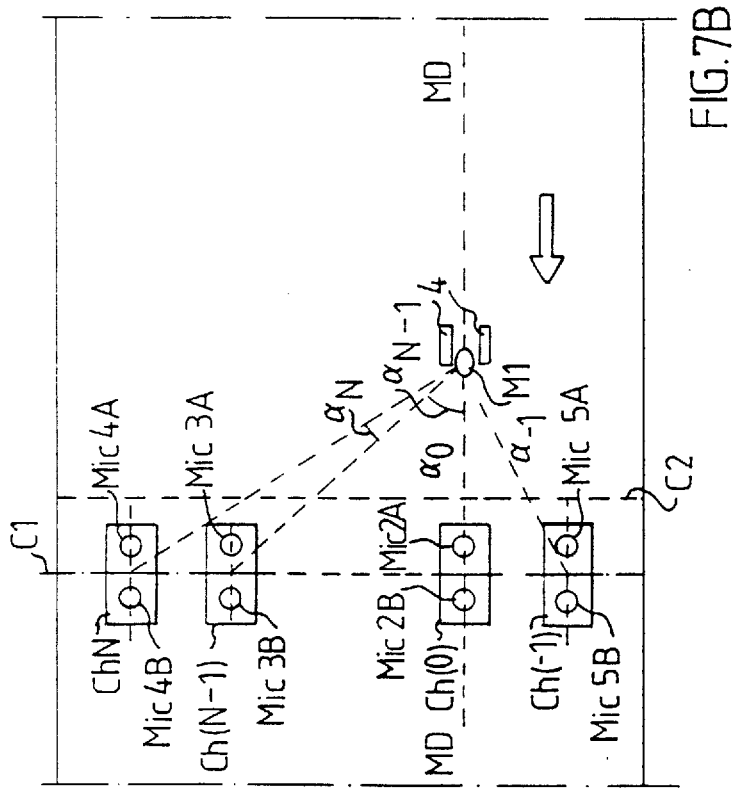

As is apparent from FIG. 7B, several sets of microphones Mic3A, Mic3B; Mic4A, Mic4B etc are shown located parallel to each other and oblique to the microphone M1 in relation to the machine direction (the respective angular directions $\alpha_{N-1}$, $\alpha_N$ etc), such that each microphone Mic3A, Mic4A is situated tangentially in the same location above the rotating cylinder 3 as the microphone Mic2A. The delay time of the symmetrical Lamb wave propagating in that oblique direction, $\alpha_{N-1}$, $\alpha_N$ etc, is measured in the same way as described above for the ultrasonic Lamb wave propagation in the machine direction, account being taken of the somewhat longer propagation path for each set.

Instead of providing an array of receiving pick-up microphone sets only one set need be provided, said set being movable along the cylinder above the web so as to be put in different oblique positions, i.e. scanning along the line C1. In this case, it is important to place the set of microphones, accurately in precise positions above the web (same distance to the web and along line C1) in order to have the same measuring conditions for each measured oblique setting (not shown in a separate figure, however the pick-up microphone set will be placed in the same way as shown in FIG. 7B).

Another embodiment shown in FIG. 7C, has only one pick-up microphone set Mic2A', Mic2B' and moves, as a unit, friction head 4 and reference microphone M1 across the web, for instance along a straight line F1 parallel to the line C1, as shown, and derives the delay time for the $s_0$ wave for a chosen amount of settings of the unit 4,M1 having different angular positions in relation to the pick-up microphone set. It is also possible to move the friction-head/microphone set 4, M1 along a curved line F2 (dashed), or to provide the velocity measurement along the machine direction separately and the measurements in the oblique directions along a line F3 (dot/dashed) perpendicular to the line C1.

It should be noted that, even for the embodiments having scanning elements along a line and one element constantly in the same position, each measuring result is provided having both kinds of elements in the same position in relation to each other during the time it takes to get the measuring result.

Many different kinds of numerical methods may be used to provide a quite precise guess about the $s_0$ wave rate in the cross direction of the paper web. One method is to fit the measured so wave rates for the different oblique positions in some kind of periodic function, e.g. the function for an ellipse or some kind of Fourier serie.

Example in which a trigonometric first order Fourier series is used:

We assume that the ultrasonic velocity of the $s_0$ wave has been measured in three different directions and these three different values are used for determining constants a0, a1 and b1. The constants are then inserted in the following formula:

$$f(\alpha) = a0 + a1 * \cos 2\alpha + b1 * \sin 2\alpha \quad (1)$$

The estimated velocity is also dependent on formula 2:

$$f(x) = k1 * x + k2 \text{ (where } x = f(\alpha)\max/f(\alpha)\min\text{)} \quad (2)$$

The constants k1 and k2 are known. A combination of the functions 1 and 2 will give the following function which determines the so wave velocity in the cross direction ($\alpha = 90°$).

$$v(CD) = f(x) * (a0 - a1) \quad (3)$$

By changing the constants k1 and k2 it is possible to get the velocity in any direction from the formula 4:

$$v(\alpha, \max/\min) = (k1(\alpha) * x + k2(\alpha)) * (a0 + a1 * \cos 2\alpha + b1 * \sin 2\alpha) \quad (4)$$

Figure 7D:
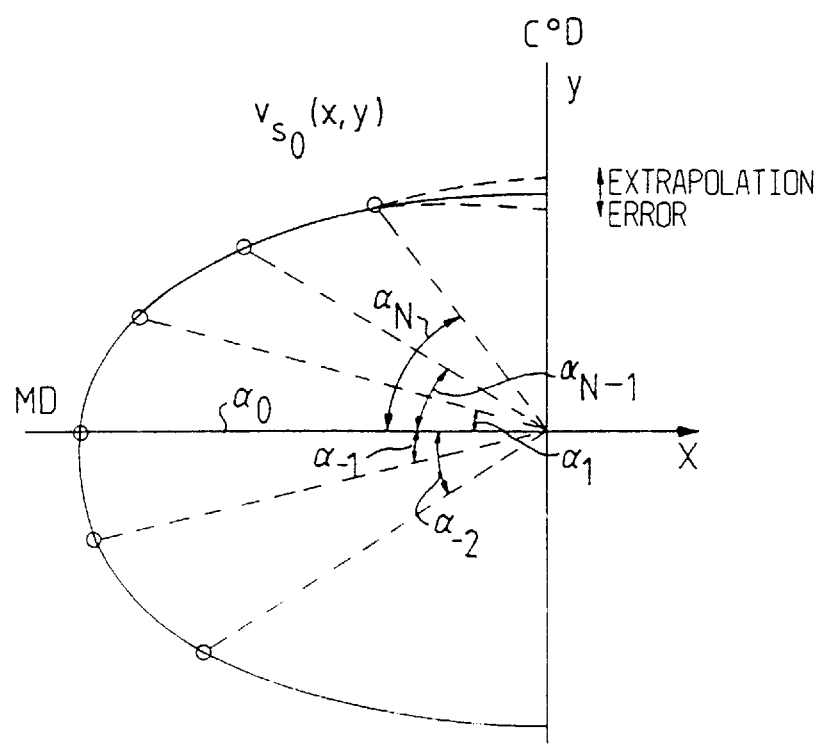
FIG. 7D illustrates a graph to provide an extrapolated value of the ultrasound velocity in the cross direction.

Another advantageous way to derive the velocity of the $s_0$ wave in the cross direction from the results from the different settings of the friction-head/reference-microphone and the pick-up microphones in relation to each other is to set the measuring results of the so wave rates in a coordinate system, with the rate in the machine direction along the X-axis and the rate in the cross direction of the web along the Y-axis, in relation to the respective angular deviation $\alpha_{N-1}$, $\alpha_N$ etc of each set to the machine direction in the way shown in FIG. 7D. A curve is drawn through the different measuring results and extrapolated to cut the Y-axis in order to provide the velocity of the so wave in the web in the cross direction. A small extrapolation error is unavoidable but is minimized by having a lot of settings of the friction-head/reference-microphone in relation to the pick-up microphones—the more, the better.

The same extrapolation technique as shown in FIG. 7D can be used also for the embodiments shown in FIG. 7C.

While the invention has been described with reference to specific embodiments, it will be understood by those skilled in the art that various changes may be made and equivalents may be substituted for elements thereof without departing from the scope of the invention as apparent from the Claims. In addition, modifications may be made without departing from the essential teachings of the invention. For instance, more than two pick-up microphones could be provided at the rotating cylinder.

We claim:

1. A system for measuring ultrasonically the elastic properties of a moving paper web, comprising:

a. means for generating a noise type ultrasonic sound wave in the web at an excitation point;

b. reference ultrasonic wave receiving means for receiving contactlessly a reference ultrasonic wave reradiated into the air from the excitation point;

c. pick-up ultrasonic wave receiving means for receiving ultrasonic wave reradiated from the paper web a predetermined distance from the location of the ultrasonic wave generating means for use in determining the elastic properties of the moving paper web, wherein the ultrasonic sound generating means and the reference ultrasonic wave receiving means are provided on the same side of the paper web; and wherein either the reference ultrasonic wave receiving means comprises one receiving element and the ultrasonic wave generating means comprises a number of elements for generating a noise type of ultrasonic wave in the web provided symmetrically around the receiving element, or the ultrasonic wave generating means comprises one element for generating a noise type ultrasonic wave in the web and the reference ultrasonic wave receiving means comprises a number of receiving elements provided symmetrically around the ultrasonic wave generating element.

2. A system according to claim 1, wherein the number is even and the means having said even number of elements has the elements arranged pairwise such that the elements in each pair have equal distances to the one element of the other means.

3. A system according to claim 1, wherein the ultrasonic wave generating means includes said number of elements;

and all said elements are provided at the side of a line through the receiving element of the reference ultrasonic wave receiving means directed in the machine direction of the moving paper web.

4. A system according to claim 1, wherein the ultrasonic wave generating means includes at least two hard dry friction contact elements in contact with the moving paper web for generating a noise type of ultrasonic wave in the web, a contact dimension perpendicular to the direction of the moving paper web and a distance between the friction contact parts being much less than a wavelength of the ultrasonic wave to be indicated generated in the paper web; and wherein the receiving element of the reference ultrasonic wave receiving means is located in between the friction contact elements.

5. A system according to claim 4, wherein the friction contact elements are made of hard alloy material and comprise tips contacting the web covered by a material absorbing ultrasonic waves.

6. A system according to claim 4, wherein each friction contact element of the ultrasonic wave generating means on parts turned from the paper web is covered by a noise shield protecting the reference ultrasonic wave receiving means from dust caused by friction between each friction contact element and the web.

7. A system according to claim 1, wherein the pick-up ultrasonic wave receiving means is located above and close to a rotating cylinder of the paper-making machine provided under the web and is positioned, relative to a direction of movement of the web from the ultrasonic wave generating means towards the rotating cylinder, at a predetermined location downstreams from a line where the moving web first touches a roll surface of the cylinder; and further comprising a first noise shield located near the pick-up ultrasonic wave receiving means for shielding the pick-up ultrasonic wave receiving means from airborne noise, the edge of the first shield turned from the pick-up ultrasonic wave receiving means being located in said direction of movement downstream from the line where the moving web first touches the cylinder, and the ultrasonic wave element(s) of the pick-up ultrasonic wave receiving means is (are) placed close to an edge of the shield turned towards the pick-up ultrasonic wave receiving means.

8. A system according to claim 7, further comprising a second noise shield located between the ultrasonic wave generating means and the pick-up ultrasonic wave receiving means for shielding the pick-up ultrasonic wave receiving means from sound and dust generated from the ultrasonic wave generating means.

9. A system according to claim 1, wherein a lateral dimension of the receiving elements of the reference ultrasonic wave receiving means are at least 10 times less than a wavelength of the ultrasonic wave in the paper web, and the receiving elements of the reference ultrasonic wave receiving means are placed at a distance from the web less than a wavelength of the ultrasonic wave reradiated from the paper web.

10. A system according to claim 1, wherein the pick-up ultrasonic wave receiving means comprises at least two adjacent pick-up elements to receive contactlessly the ultrasonic wave generated in the web by the ultrasonic wave generating means and reradiated by the web; processing means to combine outputs from the at least two pick-up receiving elements; computing means for processing outputs from the reference ultrasonic waver receiving means and from the processing means, and determining a delay time between these outputs.

11. A system according to claim 10, wherein a distance between the adjacent pick-up elements, in a plane parallel to the paper web, is half of the wavelength in air at the centre frequency of a band width used for measurements.

12. A system according to claim 1, wherein the ultrasonic wave receiving means are placed along a straight line in a machine direction of the moving paper web, which is the direction directed from the ultrasonic wave generating means towards the pick-up ultrasonic wave receiving means, in order to obtain a time between generation of the ultrasound wave part of interest to monitor and propagating in the web and the reradiation of the same wave at pick-up elements of the pick-up ultrasonic wave receiving means in order to derive Tensile Stiffness Index in the machine direction.

13. A system according to claim 1, wherein the pick-up ultrasonic wave receiving means can be oriented obliquely in relation to the reference ultrasonic wave receiving means at chosen angle(s) to a machine direction of the moving paper web, which is a direction directed from the ultrasonic wave generating means towards the pick-up ultrasonic wave receiving means, in order to obtain a time between generation of the ultrasound wave part of interest to monitor and propagating in the web and the reradiation of the same wave at receiving elements of the pick-up ultrasonic wave receiving means in order to derive the Tensile Stiffness Index in an oblique direction.

14. A system according to claim 13, wherein results from measurements in several oblique directions are combined to derive the Tensile Stiffness Index in a cross direction of the paper machine.

15. A system according to claim 10, wherein the computing means determines the delay time as a zero-cross of the Hilbert transform of a cross-correlation function between the outputs of the pick-up ultrasonic wave receiving means and the processor, corresponding to the maximum value of the cross-correlation function.

16. A system according to claim 15, wherein a Hilbert window is created in the time domain and is shifted until a peak location in time of the cross-correlation function is found and a sharp peak is derived.

* * * * *